United States Patent
Huang et al.

(10) Patent No.: US 9,702,846 B2
(45) Date of Patent: Jul. 11, 2017

(54) BIOSENSOR DEVICE AND RELATED METHOD

(71) Applicant: Taiwan Semiconductor Manufacturing Company, Ltd., Hsin-Chu (TW)

(72) Inventors: Jui-Cheng Huang, Hsin-Chu (TW); Yi-Shao Liu, Zhubei (TW); Chun-Wen Cheng, Zhubei (TW); Tung-Tsun Chen, Hsin-Chu (TW); Chin-Hua Wen, Toufen Township (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 453 days.

(21) Appl. No.: 14/075,813

(22) Filed: Nov. 8, 2013

(65) Prior Publication Data

US 2015/0129936 A1    May 14, 2015

(51) Int. Cl.
*G01N 27/414* (2006.01)

(52) U.S. Cl.
CPC ................................. *G01N 27/4145* (2013.01)

(58) Field of Classification Search
CPC ................................................. G01N 27/4145
See application file for complete search history.

(56) References Cited

U.S. PATENT DOCUMENTS

| | | | | |
|---|---|---|---|---|
| 6,046,594 | A | * | 4/2000 | Mavretic ................ G01N 27/66 324/520 |
| 9,417,257 | B2 | * | 8/2016 | Butters ................ G01N 37/005 |
| 2004/0174154 | A1 | * | 9/2004 | Butters ................ G01N 37/005 324/71.1 |
| 2004/0234417 | A1 | * | 11/2004 | Schienle ............ G01N 21/6454 422/82.08 |
| 2006/0119362 | A1 | | 6/2006 | Kermani |
| 2007/0031971 | A1 | * | 2/2007 | Kawai ................ G01N 27/3273 436/43 |
| 2007/0114443 | A1 | * | 5/2007 | Baltz .................. G01N 21/6408 250/458.1 |
| 2008/0107282 | A1 | * | 5/2008 | Asada ................ G10K 11/1782 381/71.14 |

(Continued)

FOREIGN PATENT DOCUMENTS

| | | |
|---|---|---|
| CN | 101410048 A | 4/2009 |
| CN | 103189741 A | 7/2013 |

(Continued)

OTHER PUBLICATIONS

Chen, Kuan-I, et al., "Silicon nanowire field-effect transistor-based biosensors for biomedical diagnosis and cellular recording investigation," Nano Today (2011) 6, pp. 131-154, Elsevier Ltd.

(Continued)

*Primary Examiner* — Melanie Y Brown
(74) *Attorney, Agent, or Firm* — Slater Matsil, LLP (57) ABSTRACT

A device includes a biosensor, a sensing circuit electrically connected to the biosensor, a quantizer electrically connected to the sensing circuit, a digital filter electrically connected to the quantizer, a selective window electrically connected to the digital filter, and a decision unit electrically connected to the selective window.

20 Claims, 7 Drawing Sheets

(56) References Cited

U.S. PATENT DOCUMENTS

| | | | | |
|---|---|---|---|---|
| 2009/0027040 | A1* | 1/2009 | Kermani | G01N 27/3273 324/123 R |
| 2009/0098657 | A1* | 4/2009 | Blais | A61B 5/14532 436/147 |
| 2010/0191085 | A1* | 7/2010 | Budiman | A61B 5/14532 600/365 |
| 2013/0266482 | A1* | 10/2013 | Hironaka | G01N 33/66 422/82.01 |
| 2013/0267859 | A1* | 10/2013 | Okuda | A61B 5/0245 600/500 |
| 2015/0073718 | A1* | 3/2015 | Elder | G01N 33/49 702/19 |

FOREIGN PATENT DOCUMENTS

| | | |
|---|---|---|
| JP | 2010112888 A | 5/2010 |
| TW | 201006436 | 2/2010 |
| TW | 201106920 | 3/2011 |

OTHER PUBLICATIONS

Kim, Seong-Jin et al., "Label-Free CMOS Bio Sensor With On-Chip Noise Reduction Scheme for Real-Time Quantitative Monitoring of Biomolecules." IEEE Transactions on Biomedical Circuits and Systems, vol. 6, No. 3, Jun. 2012, 8 pgs., IEEE.

Lee, Byunghun, et al., "An Electronic DNA Sensor Chip using Integrated Capacitive Readout Circuit," 32nd Annual International Conference of the IEEE EMBS, 2010, 4 pgs.

Lee, Kang-Ho, et al., "CMOS Capacitive Biosensor with Enhanced Sensitivity for Label-Free DNA Detection," 2012 IEEE International Solid-State Circuits Conference, Session 6, Medical, Displays, and Imagers, 6.6, 3 pgs.

Nakazato, Kazuo, "An Integrated ISFET Sensor Array," Sensors, 9, pp. 8831-8851.

* cited by examiner

BIOSENSOR DEVICE AND RELATED METHOD

BACKGROUND

The semiconductor industry has experienced rapid growth due to improvements in the integration density of a variety of electronic components (e.g., transistors, diodes, resistors, capacitors, etc.). For the most part, this improvement in integration density has come from shrinking the semiconductor process node (e.g., shrinking the process node towards the sub-20 nm node). Another semiconductor industry experiencing rapid growth is the microelectromechanical systems (MEMS) industry. MEMS devices are found in a variety of applications, ranging from automotive electronics to smartphones, and even biomedical devices.

Biomedical MEMS (BioMEMS) devices perform a variety of functions. A pH sensor is one type of BioMEMS device that electronically determines pH of a solution in contact with the pH sensor. The pH sensor may be used in disease detection, organ tissue monitoring, water contamination identification, or myriad other practical applications.

BRIEF DESCRIPTION OF THE DRAWINGS

For a more complete understanding of the present embodiments, and the advantages thereof, reference is now made to the following descriptions taken in conjunction with the accompanying drawings, in which.

DETAILED DESCRIPTION OF ILLUSTRATIVE EMBODIMENTS

The making and using of the present embodiments are discussed in detail below. It should be appreciated, however, that the present disclosure provides many applicable inventive concepts that can be embodied in a wide variety of specific contexts. The specific embodiments discussed are merely illustrative of specific ways to make and use the disclosed subject matter, and do not limit the scope of the different embodiments.

Embodiments will be described with respect to a specific context, namely biosensor circuits and related methods. Other embodiments may also be applied, however, to other types of sensing circuits.

Throughout the various figures and discussion, like reference numbers refer to like objects or components. Also, although singular components may be depicted throughout some of the figures, this is for simplicity of illustration and ease of discussion. A person having ordinary skill in the art will readily appreciate that such discussion and depiction can be and usually is applicable for many components within a structure.

In the following disclosure, a novel biosensor system and method are introduced. The biosensor system uses a digital filter and selective window to increase signal-to-noise resolution (SNR). The biosensor system optionally includes a feedback network and tuning circuit for performing self-calibration.

Figure 1:
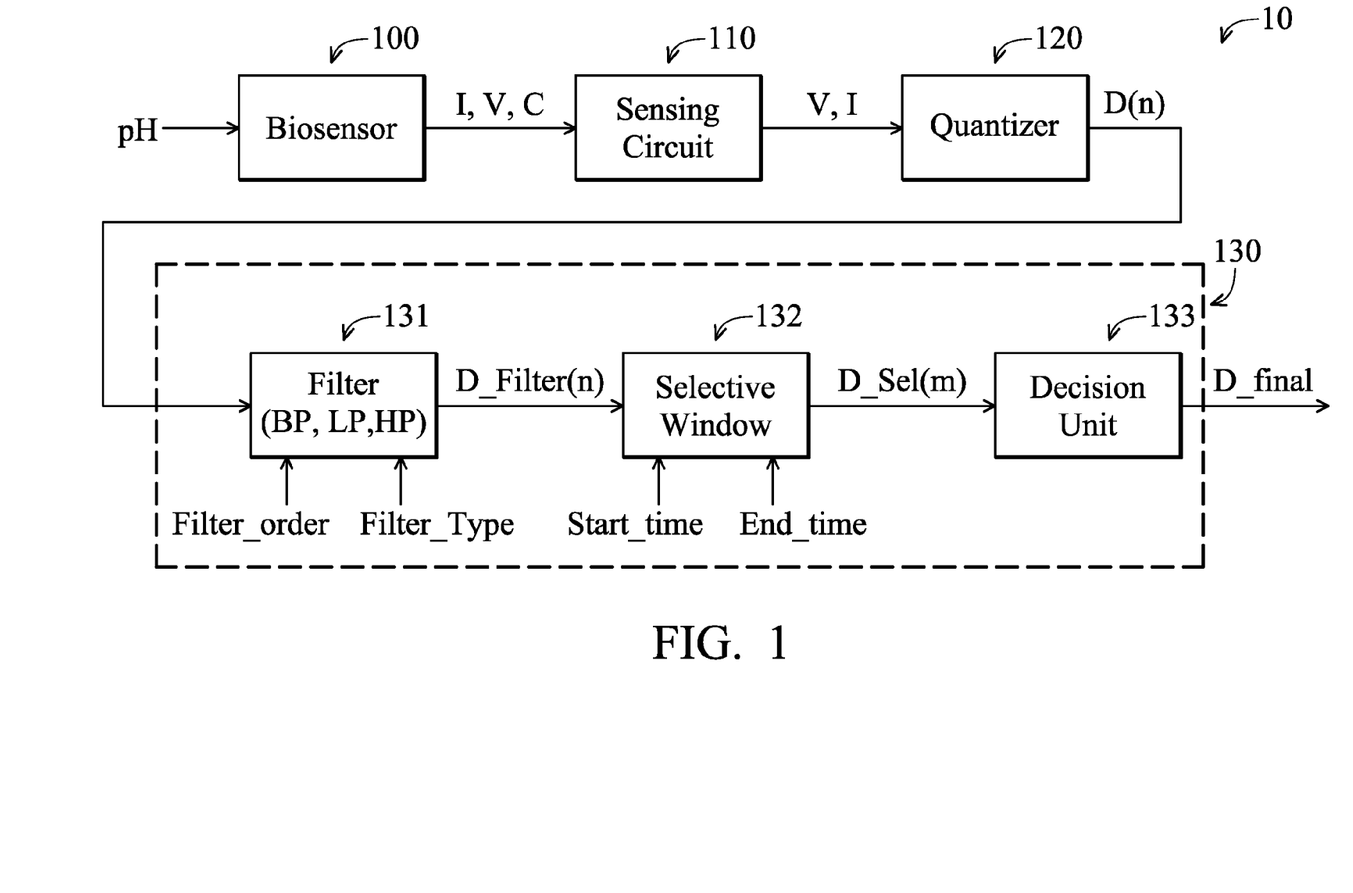
FIG. 1 is a diagram showing a biosensor system in accordance with various embodiments of the present disclosure.

FIG. 1 is a diagram showing a biosensor system 10 in accordance with various embodiments of the present disclosure. A biosensor 100 of the biosensor system 10 senses a parameter (e.g., pH) of a solution, and outputs an according signal (e.g., current, voltage, capacitance, or the like). In some embodiments, the biosensor 100 is one of an array of biosensors. In some embodiments, the biosensor 100 is an ion-sensitive field effect transistor (ISFET), a nanowire, a nanopore, or the like. In some embodiments, the biosensor system 10 is integrated into a single integrated circuit (IC).

A sensing circuit 110 is electrically connected to the biosensor 100. In some embodiments, the sensing circuit 110 includes a multiplexer for selecting the biosensor 100 from the array of biosensors. In some embodiments, the sensing circuit 110 includes a converter. In some embodiments, the converter is a current-to-voltage converter, a voltage-to-voltage converter, a capacitance-to-voltage converter, or the like. In some embodiments, the converter converts an input signal (e.g., current, voltage, capacitance) to a current. In some embodiments, the sensing circuit 110 further includes an amplifier.

A quantizer 120 is electrically connected to the sensing circuit 110. In some embodiments, the quantizer 120 includes an analog-to-digital converter (ADC). In some embodiments, the ADC is a voltage-mode ADC, a current-mode ADC, or the like. The quantizer 120 receives an analog output signal of the sensing circuit 110 (e.g., voltage, current), and generates a digital output signal D(n) representing the analog output signal. In some embodiments, the digital output signal D(n) includes an integer number of digital bits. In some embodiments, the quantizer 120 includes a register for storing and outputting the digital bits.

In many biosensing applications, settling time of an output signal of the biosensor 100 (e.g., voltage, current, capacitance), and by extension the digitized version of the output signal (or, "digital signal"), is very long relative to output signals of traditional sensors. Limitations on biosensor performance include chemical flow, bio-reaction, bio-sample, and detection methods. For example, a pH detector may require about 30 seconds or longer to output a stable voltage due to at least one of the above factors. The digital signal representing the pH of a solution further includes noise. The noise may include high-frequency noise (thermal or shot noise), and low frequency noise (long-term drift, ion diffusion, or pixel-to-pixel crosstalk). The noise sources are not easily characterized, and noise phenomena are generally unique for each pairing of biosensor and chemical solution.

As a result, a post-processing subsystem 130 is electrically connected to the quantizer 120. A digital filter 131 is electrically connected to the quantizer 120. In some embodiments, the digital filter 131 includes a low-pass filter, a high-pass filter, a bandpass filter, or the like. In some embodiments, the digital filter 131 includes a finite impulse response (FIR) filter. In some embodiments, the digital filter 131 includes a moving average filter. In some embodiments, a first digital signal Filter_Type is inputted to the digital filter 131 to select a type (e.g., bandpass, low-pass, high-pass) of the digital filter 131. In some embodiments, a digital signal Filter_order is used to select an order (e.g., first-order, second-order, etc.) of the digital filter 131. The digital filter 131 outputs a filtered digital signal D_Filter(n). The filtered digital signal D_Filter(n) is a filtered version of the digital output signal D(n), where type and order of filtering depend on electrical configuration or design of the digital filter 131.

The filtered digital signal D_Filter(n) is received by a selective window 132 electrically connected to an output terminal of the digital filter 131. The selective window 132 is a digital circuit that outputs a selected signal D_Sel(m) from the filtered digital signal D_Filter(n). The selected signal D_Sel(m) includes a sequence of bits of the filtered digital signal D_Filter(n) that corresponds to a settled region of the filtered digital signal D_Filter(n). In some embodiments, the sequence of bits is a time-shifted sequence of bits of the filtered digital signal D_Filter(n). For example, the filtered digital signal D_Filter(n) may include digital data corresponding to a period from about when the biosensor 100 begins sensing pH of a solution (time t1) to about when the biosensor 100 stops sensing the pH of the solution (time t2). The duration of time between the time t1 and the time t2 may be about 1 minute, as an example. The selected signal D_Sel(m) may capture a window of the digital data starting from a time t3 to a time t4. The time t3 is a first period after the time t1, and the time t4 is a second period before the time t2. In some embodiments, the time t4 is simply the time t2. In some embodiments, the first period is greater than about 10 seconds. In some embodiments, the first period is greater than about 30 seconds.

In some embodiments, the selective window 132 receives at least a start time signal Start_time. In some embodiments, the selective window 132 further receives an end time signal End_time. For example, the start time signal Start_time may be a digital code representing 30 seconds, and the end time signal End_time may be a digital code representing 40 seconds. In some embodiments, the selective window 132 receives a duration signal. For example, the start time signal Start_time may be a digital code representing 30 seconds, and the duration signal may be a digital code representing 10 seconds.

In some embodiments, the start time signal Start_time is a rising edge generated a predetermined delay period after beginning sensing by the biosensor 100. For example, the biosensor 100 may receive an enable signal at the time t1 to begin sensing the pH of the solution. The enable signal may be received by a counter. When the counter outputs a first count signal corresponding to the predetermined delay period (e.g., 30 seconds), a decoder receiving the count signal may output a rising edge as the start time signal Start_time. When the counter outputs a second count signal corresponding to the first period plus a sampling period (e.g., 30 seconds plus 10 second), the decoder receiving the second count signal may output a second rising edge as the end time signal End_time.

In some embodiments, the selective window 132 samples the filtered digital signal D_Filter(n) to generate the selected signal D_Sel(m) by an automated process. For example, a variation threshold may be stored in a register. The selective window 132 may compare a first value of the filtered digital signal D_Filter(n) with a second value of the filtered digital signal D_Filter(n). When a difference between the second value and the first value is less than the variation threshold, the selective window 132 may begin capturing the selected signal D_Sel(m). For example, when detecting the pH of the solution, when the first value is greater than the second value by less than about 0.05 (on the pH scale), the selective window 132 may begin capturing the selected signal D_Sel(m).

In some embodiments, the biosensor system 10 is a medical test system for determining a medical condition (e.g., positive or negative for a virus, or the like). A decision unit 133 has an input terminal electrically connected to an output terminal of the selective window 132. The decision unit 133 receives the selected signal D_Sel(m), and generates a decision signal D_final according to value of the selected signal D_Sel(m). For example, if a pH range corresponds to a positive reading for a certain virus, the decision signal D_final may have logical value one or high when the selected signal D_Sel(m) is within the pH range. In some embodiments, the decision unit 133 includes a digital comparator for comparing the selected signal D_Sel(m) with a reference value. In some embodiments, the reference value is a digital code having a first number of bits equal to a second number of bits of the selected signal D_Sel(m). For example, if the selected signal D_Sel(m) is an m-bit signal, the reference value may include m bits.

Figure 2:
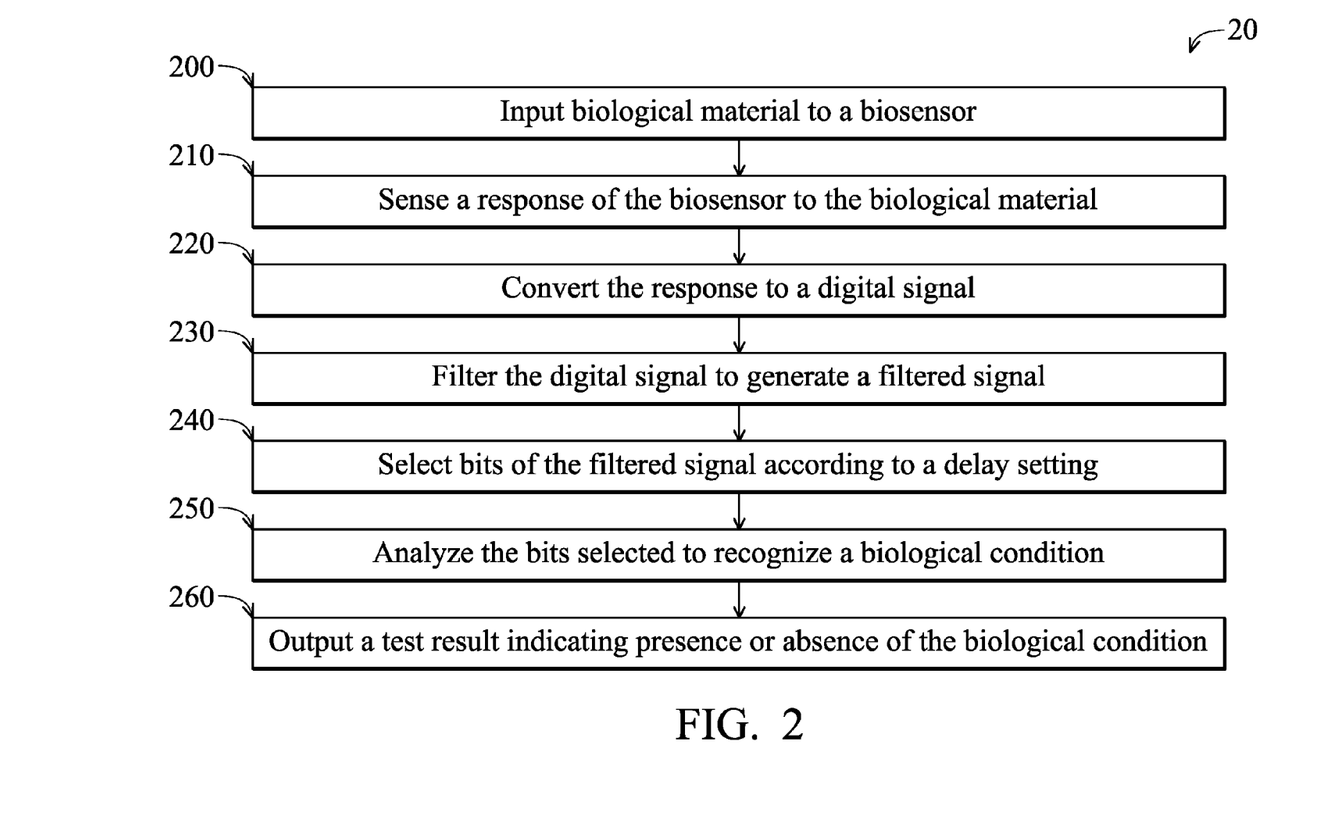
FIG. 2 is a flowchart of a method in accordance with various embodiments of the present disclosure.

FIG. 2 is a flowchart of a method 20 in accordance with various embodiments of the present disclosure. The method 20 is compatible with the biosensor system 10, and can be used to test a biological substance for a biological condition. Biological material (e.g., a solution) is inputted 200 to a biosensor, such as the biosensor 100. The biosensor responds to contact of the biological material with a sensing region of the biosensor. For example, the solution may contact a front gate of an ISFET, which changes threshold voltage of the ISFET, and alters output current of the ISFET. A response of the biosensor to the biological material is sensed 210. In some embodiments, the response is a voltage signal, a current signal, a capacitance signal, or the like. The response is converted 220 to a digital signal. In some embodiments, the conversion 220 is performed by an ADC (voltage mode or current mode).

Post-processing 230-260 is performed on the digital signal to generate a test result. The digital signal is filtered 230 to generate a filtered signal (e.g., the filtered digital signal D_Filter(n)). In some embodiments, the filtering 230 includes low-pass filtering, high-pass filtering, bandpass filtering or the like. Bits of the filtered signal are selected 240 according to a delay setting. In some embodiments, a stream of bits is generated by the conversion 220, the stream of bits is filtered by the filtering 230, and the filtered bits are stored in a register. Then, an intermediate subset of the stream of bits (e.g., a $1024^{th}$ bit through a $2048^{th}$ bit) is selected 240. The intermediate subset corresponds to the delay setting. In some embodiments, the filtered bits begin to be stored at a clock edge of a selection signal. The clock edge may be delayed from a beginning of sensing 210 by a predetermined delay (e.g., about 30 seconds).

The bits selected by selecting 240 are analyzed 250 to recognize a biological condition. For example, the bits may be compared with a pH value. If value of the bits is substantially equal to (or within a predetermined range around) the pH value, the biological condition is recognized as positive or negative. Presence or absence of the biological condition (positive or negative screener) is indicated by outputting 260 a test result. In some embodiments, the outputting 260 includes altering a digital display (e.g., a light-emitting diode, a pixel array, or the like), emitting an audible noise, or the like. In some embodiments, the outputting 260 includes outputting a true or false indicator. In some embodiments, the outputting 260 includes outputting a number corresponding to, for example, severity of the biological condition.

Figure 3:
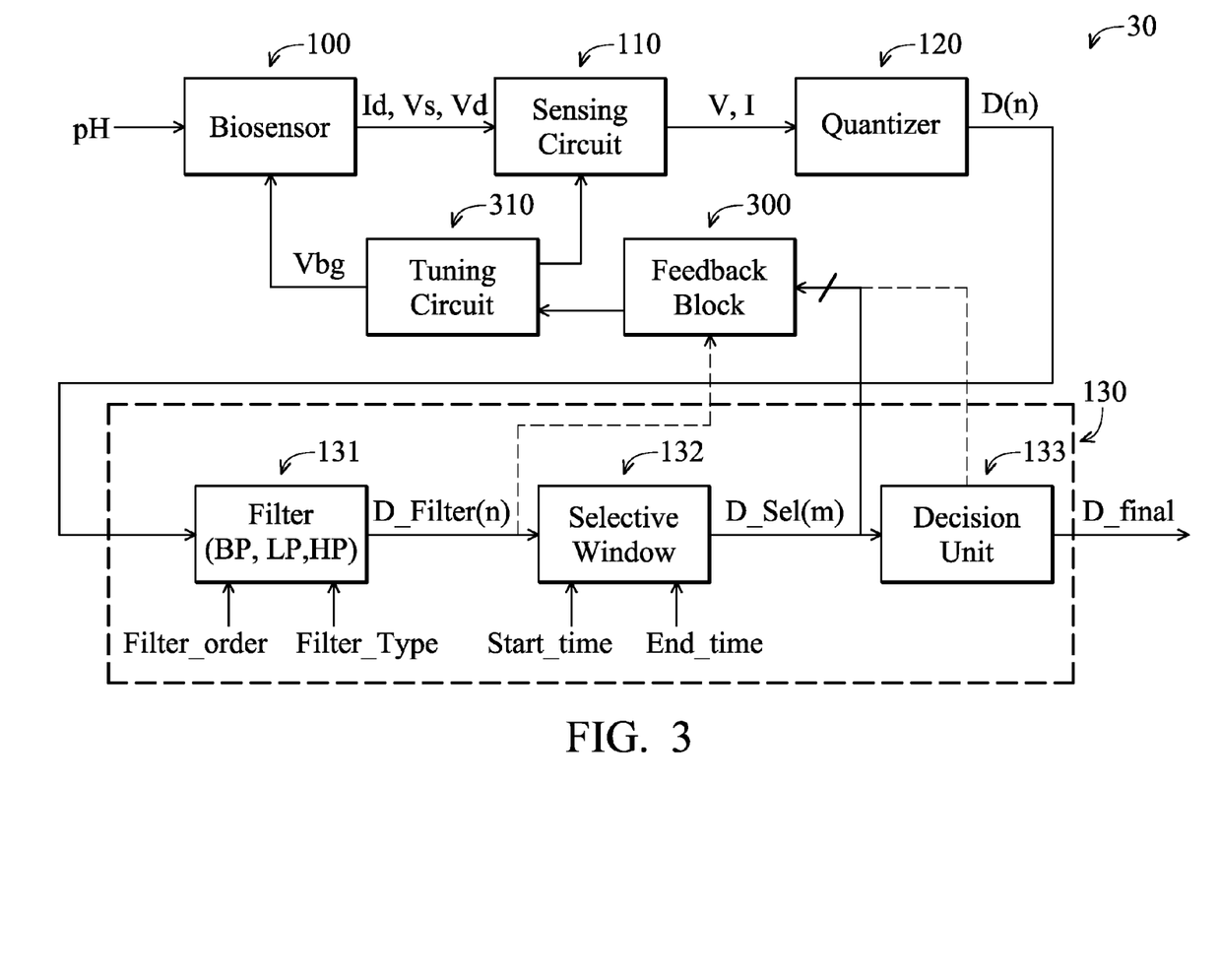
FIG. 3 is a circuit block diagram showing a biosensor system with internal calibration in accordance with various embodiments of the present disclosure.

FIG. 3 is a circuit block diagram showing a biosensor system 30 with internal calibration in accordance with various embodiments of the present disclosure. The biosensor system 30 is similar in many respects to the biosensor system 10, and like reference numerals refer to like blocks in FIG. 3 and FIG. 1. In some embodiments, the biosensor system 30 includes a feedback block 300 and a tuning circuit 310.

In some embodiments, the feedback block 300 includes a wire, a buffer, other logic gates, or the like. In some embodiments, the feedback block 300 includes parallel inputs (e.g., a 4-bit, 8-bit, or greater number of bits bus). The feedback block 300 provides a path for the tuning circuit 310 to receive digital bits generated from the digital signal D(n). In some embodiments, an input terminal(s) of the feedback block 300 is electrically connected to an output terminal(s) of the selective window 132 for receiving the selected signal D_Sel(m). In some embodiments, the input terminal(s) of the feedback block 300 is electrically connected to an internal node(s) of the decision unit 133. In some embodiments, the input terminal(s) of the feedback block 300 is electrically connected to the output terminal(s) of the filter 131 for receiving the filtered signal D_Filter(n).

In some embodiments, the tuning circuit 310 adjusts biasing conditions of the biosensor 100 or the sensing circuit 110 based on the digital bits received through the feedback block 300. In some embodiments, the tuning circuit 310 has an output terminal electrically connected to a reference voltage supply that generates the back gate voltage Vbg biasing the back gate electrode of the biosensor 100. In some embodiments, the tuning circuit 310 calibrates the biosensor 100 by increasing or decreasing sensitivity of the biosensor 100 through altering the back gate voltage Vbg. In some embodiments, the tuning circuit 310 has an output terminal electrically connected to a bias generator that electrically biases the sensing circuit 110. In some embodiments, the bias generator is a current supply biasing a sense amplifier of the sensing circuit 110. In some embodiments, the tuning circuit 310 calibrates the sense amplifier of the sensing circuit 110 to increase or decrease sensitivity of the sense amplifier by modifying amplitude of the current supply biasing the sense amplifier. In some embodiments, the tuning circuit 310 adjusts biasing of the biosensor 100 or the sensing circuit 110 on the basis of calibration (e.g., two-point calibration) performed using the digital bits received from the feedback block 300. The calibration may be performed, for example, by reading a first pH of a solution, capturing first digital bits generated during the reading of the first pH, reading a second pH of the solution, capturing second digital bits generated during the reading of the second pH, and performing two-point calibration using the first digital bits and the second digital bits.

Figure 4:
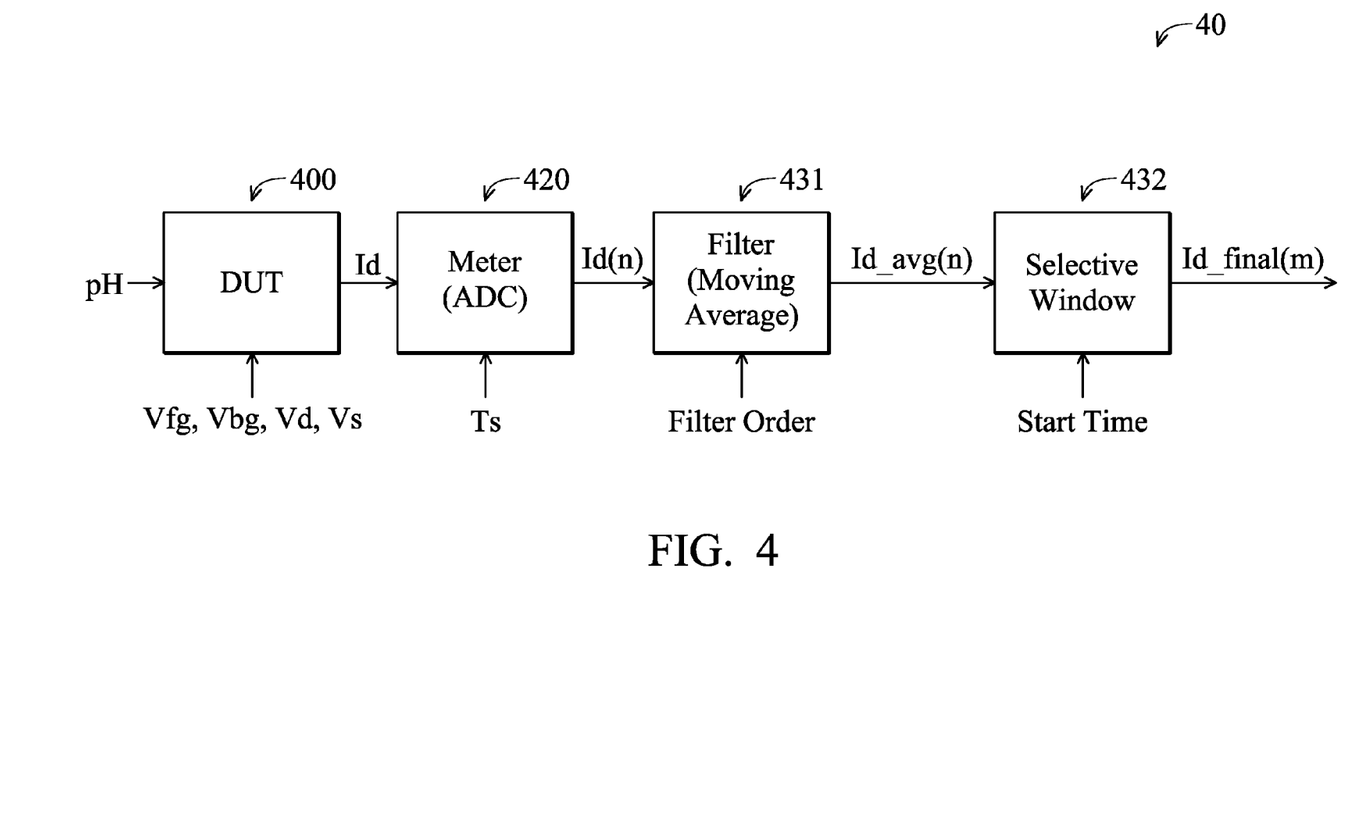
FIGS. 4, 5, and 6 are diagrams showing a calibration path, and a device under test (DUT) of the calibration path in accordance with various embodiments of the present disclosure.
Figure 5:
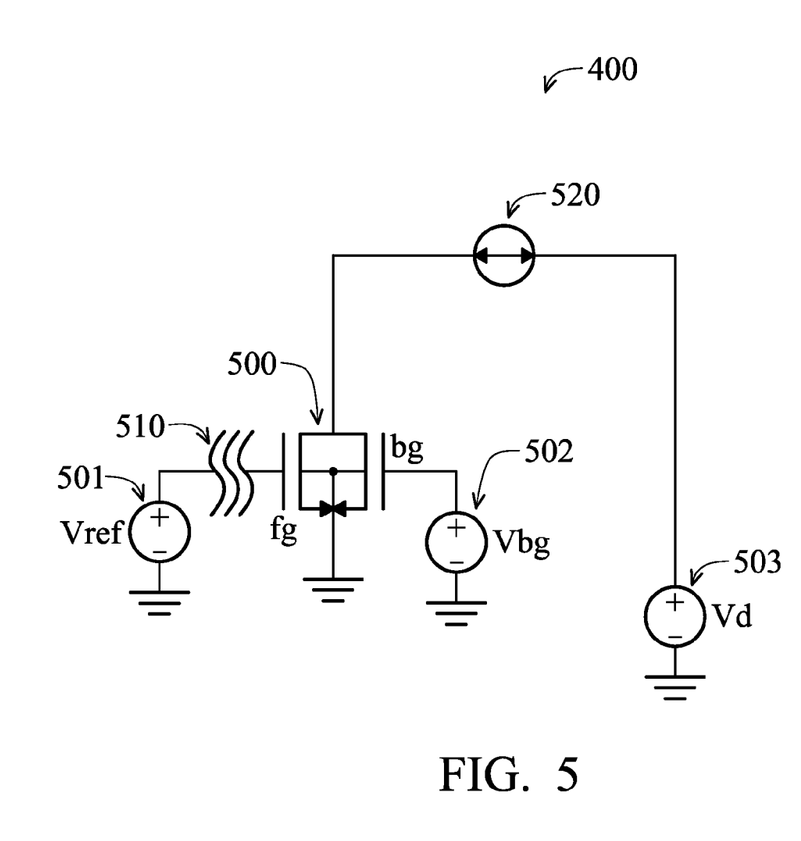
Figure 6:
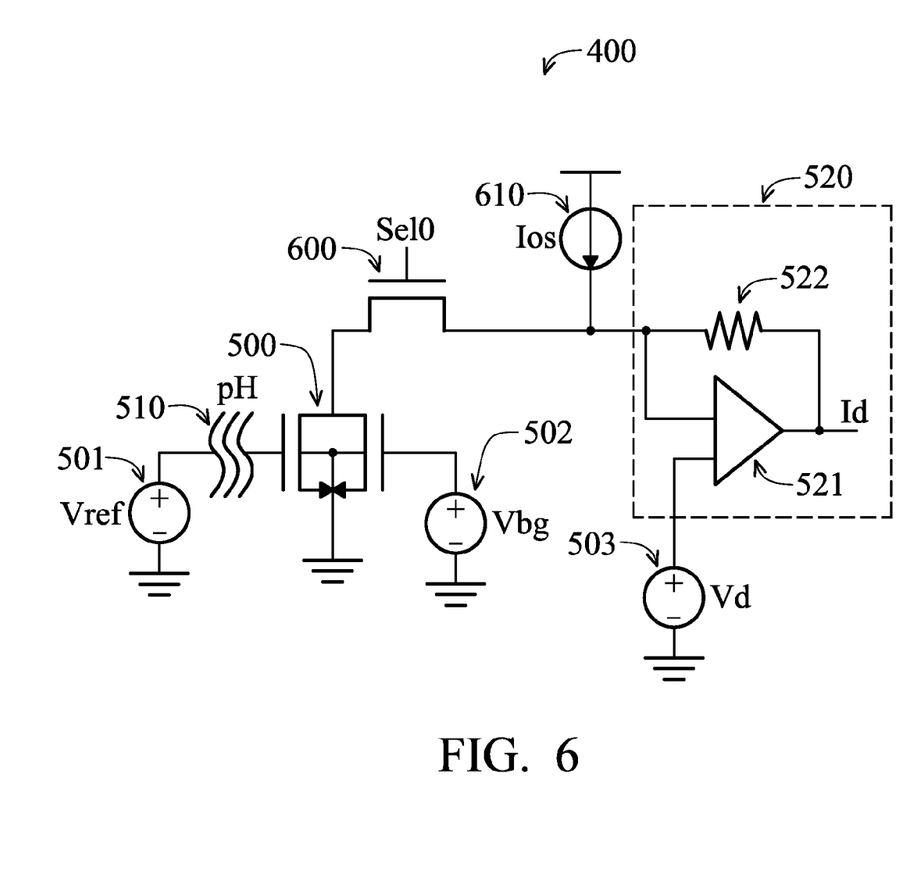

FIGS. 4, 5, and 6 are diagrams showing a calibration path 40, and a device under test (DUT) 400 of the calibration path 40 in accordance with various embodiments of the present disclosure. FIG. 4 is a circuit block diagram of the calibration path 40 in accordance with various embodiments of the present disclosure. In some embodiments, a DUT 400 is a biosensor, similar to the biosensor 100 of FIG. 1. In some embodiments, the DUT 400 is in contact with a solution having a pH. Front gate, back gate, drain and source electrodes of the DUT 400 are biased by a front gate voltage source Vfg, a back gate voltage Vbg, a drain voltage Vd, and a source voltage Vs, respectively. In some embodiments, the source voltage is ground. The DUT 400 outputs a current signal Id that is proportional to the pH of the solution.

A meter 420 of the calibration path 40 has an input terminal electrically connected to the DUT 400 for receiving the current signal Id. In some embodiments, the meter 420 is an ADC, and receives a sampling period signal Ts. The meter 420 outputs a digital current signal Id(n) at an output terminal of the meter 420. A filter 431 has an input terminal electrically connected to the output terminal of the meter 420. In some embodiments, the filter 431 is a moving average filter. In some embodiments, the filter 431 has configurable filter order. For the filter 431 being the moving average filter, the filter 431 outputs an averaged current signal Id_avg(n) at an output terminal of the filter 431. A selective window 432 receives the averaged current signal Id_avg(n) and a start time signal, and generates a selected signal Id_final(m). The selected signal Id_final(m) includes a selection of digital bits of the averaged current signal Id_avg(n). In some embodiments, a first bit of the selected signal Id_final(m) is stored substantially at a rising or falling edge of the start time signal.

FIG. 5 is a circuit diagram showing the DUT 400 of FIG. 4 in accordance with various embodiments of the present disclosure. In some embodiments, a biosensor 500 is an ISFET. A front gate (fg) of the biosensor 500 is in contact with a solution 510, and is biased by a reference voltage Vref generated by a reference voltage supply 501. A back gate (bg) of the biosensor 500 is electrically connected to a back gate voltage supply 502 that generates a back gate voltage Vbg. A source electrode of the biosensor 500 is electrically connected to a power supply node (e.g., ground). A drain electrode of the biosensor 500 is electrically connected to a current meter 520, and receives a drain voltage Vd generated by or copied from a drain bias voltage supply 503.

Threshold voltage of the biosensor 500 varies with pH of the solution 510 in contact with the front gate. For a first pH value, the biosensor 500 generates a first current in response to the reference voltage Vref. The first current is measured by the current meter 520, which generates a first signal (e.g., a voltage signal) proportional to the first current. For a second pH value different from the first pH value, the biosensor 500 generates a second current different from the first current in response to the reference voltage Vref.

FIG. 6 is a detailed circuit diagram of the DUT 400 in accordance with various embodiments of the present disclosure. In some embodiments, the biosensor 500 is one of an array of similar biosensors. For example, the biosensor 500 may be one of an array of ISFETs. To select the biosensor 500 for calibration, a select transistor 600 is electrically connected to the biosensor 500. In some embodiments, a drain electrode of the select transistor 600 is electrically connected to the drain electrode of the biosensor 500. A gate electrode of the select transistor 600 receives a control signal Sel0.

A current supply 610 that generates a current Ios is electrically connected to a source electrode of the select transistor 600. When the select transistor 600 is turned on, the biosensor 500 draws current from the current supply 610. The current drawn by the biosensor 500 is amplified by an amplifier 521 of the current meter 520. In some embodiments, a non-inverting input terminal of the amplifier 521 is electrically connected to the drain bias voltage supply 503. A virtual short causes voltage at an inverting input terminal of the amplifier 521 to be substantially equal to the drain voltage Vd. A resistor 522 has a first terminal electrically connected to an output terminal of the amplifier 521, and a second terminal electrically connected to the inverting input terminal of the amplifier 521. Resistance of the resistor 522 may be large (e.g., on the order of hundreds of KΩ).

Figure 7:
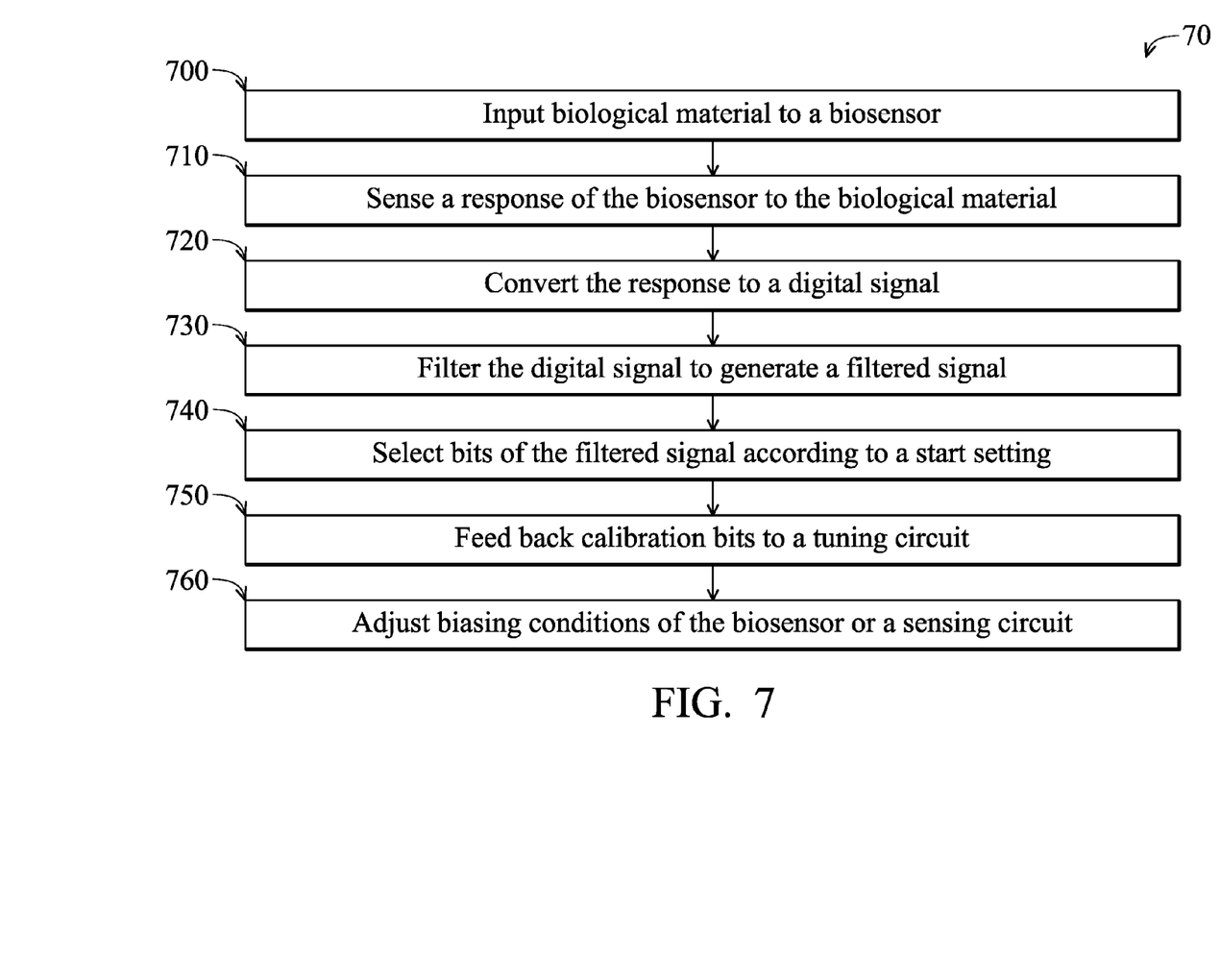
FIG. 7 is a flowchart of a method for calibrating a biosensor system in accordance with various embodiments of the present disclosure.

FIG. 7 is a flowchart of a method 70 for calibrating a biosensor system in accordance with various embodiments of the present disclosure. In some embodiments, the method 70 is used with the biosensor system 30 of FIG. 3 or the calibration path 40 of FIGS. 4-6. Biological material (e.g., a solution) is inputted 700 to a biosensor, such as the biosensor 100 or the biosensor 500. The biosensor responds to the biological material, and the response is sensed 710. In some embodiments, the response is a change in output current of the biosensor. In some embodiments, the sensing 710 is performed by a sensing circuit, such as the sensing circuit 110 or the current meter 520. In some embodiments, the sensing 710 includes amplifying, such as may be performed by the amplifier 521.

The response (or the amplified response) is converted 720 to a digital signal. In some embodiments, the conversion 720 is by an ADC. In some embodiments, the conversion 720 is performed based on a sampling period setting, a resolution setting, or the like, which is applied to the circuit (e.g., the ADC) performing the conversion 720.

The digital signal is filtered 730 to generate a filtered signal (e.g., the filtered signal D_filter(n) or the averaged current signal Id_avg(n)). In some embodiments, the filtering 730 includes low pass filtering, high pass filtering, bandpass filtering, moving average filtering, or the like.

Bits of the filtered signal are selected 740 according to a start setting. In some embodiments, the start setting is a pulse or signal edge that is delayed from when the biosensor begins sensing by a predetermined settling period (e.g., on the order of tens of seconds). In some embodiments, the start setting is a digital signal indicating bit positions (e.g., a start bit and an end bit) of the filtered signal.

Calibration bits are fed back 750 to a tuning circuit (e.g., the tuning circuit 310). In some embodiments, the feeding back 750 is by a feedback network, such as the feedback block 300. In some embodiments, the calibration bits are digital bits of the digital signal, filtered bits of the filtered signal, or selected bits of a selected signal generated by selecting 750.

Biasing conditions of the biosensor or sensing circuit are adjusted 760 based on calibration information stored in the calibration bits. In some embodiments, the adjusting 760 includes changing back gate voltage Vbg of an ISFET, or current supply applied to an amplifier (e.g., the amplifier 521) of the sensing circuit.

Embodiments may achieve advantages. Post-processing performed by the post-processing subsystem 130 smooths the digital signal read from the biosensor 100 or 500, and selects bits of the filtered signal that correspond to a more settled region of the digital signal. As a result, accuracy of the biosensor systems 10, 30 is better compared to other approaches. The feedback block 300 and tuning circuit 310 allow for fast calibration of an array of biosensors. Performing post-processing in the digital domain increases flexibility and tunability. Signal-to-noise ratio (SNR) is also improved by speed of the quantizer 120.

In accordance with various embodiments of the present disclosure, a device includes a biosensor, a sensing circuit electrically connected to the biosensor, a quantizer electrically connected to the sensing circuit, a digital filter electrically connected to the quantizer, a selective window electrically connected to the digital filter, and a decision unit electrically connected to the selective window.

In accordance with various embodiments of the present disclosure, a device includes a biosensor, a sensing circuit electrically connected to the biosensor, a quantizer electrically connected to the sensing circuit, a digital filter electrically connected to the quantizer, a selective window electrically connected to the digital filter, a feedback path electrically connected to at least one of the quantizer, the digital filter, or the selective window, and a tuning circuit electrically connected to the feedback path and at least one of the biosensor or the sensing circuit.

As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising". Moreover, the term "between" as used in this application is generally inclusive (e.g., "between A and B" includes inner edges of A and B).

Although the present embodiments and their advantages have been described in detail, it should be understood that various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A device comprising:
    a biosensor;
    a sensing circuit electrically connected to the biosensor;
    a quantizer electrically connected to the sensing circuit;
    a digital filter electrically connected to the quantizer;
    a selective window electrically connected to the digital filter; and
    a decision unit electrically connected to the selective window.

2. The device of claim 1, wherein the biosensor is an ion-sensitive field effect transistor (ISFET).

3. The device of claim 1, wherein the digital filter includes a moving average filter.

4. The device of claim 1, wherein the digital filter includes at least one of a bandpass filter, a lowpass filter, or a highpass filter.

5. The device of claim 4, wherein order of the digital filter is tunable.

6. The device of claim 4, wherein type of the digital filter is selectable.

7. The device of claim 1 further comprising a feedback path electrically connected to an output of the selective window, an internal node of the decision unit, or a combination thereof.

8. The device of claim 7 further comprising a tuning circuit configured to adjust biasing conditions of the biosensor, wherein the feedback path is electrically connected to an input of the tuning circuit.

9. The device of claim 7 further comprising a tuning circuit configured to adjust biasing conditions of the sensing circuit, wherein the feedback path is electrically connected to an input of the tuning circuit.

10. A circuit comprising:
a biosensor, wherein the biosensor senses a parameter of a solution and outputs a first signal;
a sensing circuit electrically connected to the biosensor, wherein the sensing circuit converts the first signal to a second signal;
a quantizer electrically connected to the sensing circuit, wherein the quantizer converts the second signal to a digital signal;
a post-processing subsystem electrically connected to the quantizer, wherein the post-processing subsystem comprises:
a filter, wherein the filter converts the digital signal to a filtered digital signal;
a selective window electrically connected to the filter, wherein the selective window selects a sequence of bits from the filtered digital signal; and
a decision unit, wherein the decision unit generates an output in accordance with the sequence of bits selected from the filtered digital signal;
a feedback path electrically connected to the post-processing subsystem; and
a tuning circuit, wherein the tuning circuit calibrates the biosensor, the sensing circuit, or a combination thereof in accordance with an input from the feedback path.

11. The circuit of claim 10, wherein the selective window receives a start time signal, an end time signal, a duration signal, or a combination thereof, wherein the sequence of bits is selected from the filtered digital signal in accordance with the start time signal, the end time signal, the duration signal, or the combination thereof.

12. The circuit of claim 10, wherein the selective window selects a sequence of bits from the filtered digital signal by an automated process.

13. The circuit of claim 12, wherein the sequence of bits is selected from the filtered digital signal based at least in part on comparing a difference between first bits representing a first value of the filtered signal at a first time and second bits representing a second value of the filtered signal at a second time with a variation threshold stored in a register.

14. The circuit of claim 12, wherein the feedback path is electrically connected to an output of the selective window, an internal node of the decision unit, or a combination thereof.

15. A device comprising:
a biosensor;
a sensing circuit electrically connected to the biosensor, wherein the sensing circuit is configured to output an analog signal;
a quantizer electrically connected to the sensing circuit and configured to receive the analog signal from the sensing circuit and output a digital signal;
a filter electrically connected to the quantizer and configured to receive the digital signal from the quantizer and output a filtered signal;
a selective window electrically connected to the filter and configured to receive the filtered signal from the filter and output a selected signal, wherein the selected signal comprises a portion of the filtered signal corresponding to a time duration; and
a decision unit electrically connected to the selective window and configured to receive the selected signal and output a decision signal.

16. The device of claim 15, wherein the biosensor is a first biosensor in an array comprising a plurality of biosensors, and wherein the sensing circuit is electrically connected to each biosensor in the plurality of biosensors.

17. The device of claim 15, further comprising a feedback circuit electrically connected to the selective window and a tuning circuit electrically connected to the feedback circuit and at least one of the biosensor or the sensing circuit.

18. The device of claim 15, wherein the selective window determines the time duration based at least in part on comparing a first value of the filtered signal and a second value of the filtered signal.

19. The device of claim 15, wherein the selective window is configured to receive a start time signal and the selective window determines the time duration based at least in part on the start time signal.

20. The device of claim 15, wherein the decision unit outputs a decision signal based at least in part on comparing the selected signal with a reference value.

* * * * *